United States Patent [19]
Buck et al.

[11] Patent Number: 5,803,083
[45] Date of Patent: Sep. 8, 1998

[54] GUIDING CATHETER WITH ULTRASOUND IMAGING CAPABILITY

[75] Inventors: Jerrick C. Buck, Miami; Donald J. Larnard, Boca Raton, both of Fla.

[73] Assignee: Cordis Corporation, Miami Lakes, Fla.

[21] Appl. No.: 723,821

[22] Filed: Sep. 30, 1996

Related U.S. Application Data

[60] Provisional application No. 60/006,493 Nov. 9, 1995.

[51] Int. Cl.⁶ .................................. A61B 8/00; A61N 1/05
[52] U.S. Cl. ...................... 128/660.03; 128/642; 607/122
[58] Field of Search ................... 128/642, 660.03; 607/122, 99–101; 606/37–40

[56] References Cited

U.S. PATENT DOCUMENTS

| | | |
|---|---|---|
| 4,531,943 | 7/1985 | Van Tassel et al. . |
| 4,552,554 | 11/1985 | Gould et al. . |
| 4,769,005 | 9/1988 | Ginsburg et al. . |
| 5,045,072 | 9/1991 | Castillo et al. . |
| 5,325,860 | 7/1994 | Seward et al. . |
| 5,345,940 | 9/1994 | Seward et al. ..................... 128/662.06 |
| 5,368,564 | 11/1994 | Savage . |
| 5,409,000 | 4/1995 | Imran . |
| 5,431,168 | 7/1995 | Webster, Jr. . |
| 5,487,385 | 1/1996 | Avitall . |

*Primary Examiner*—Francis Jaworski
*Attorney, Agent, or Firm*—Michael W. Montgomery

[57] ABSTRACT

A steerable guiding catheter having an ultrasound imaging distal tip for use in guiding an electrophysiology catheter. The guiding catheter includes a steering mechanism in order to steer the tip of the catheter so that the electrophysiology catheter may be steered to a desired location within the body of a patient.

6 Claims, 5 Drawing Sheets

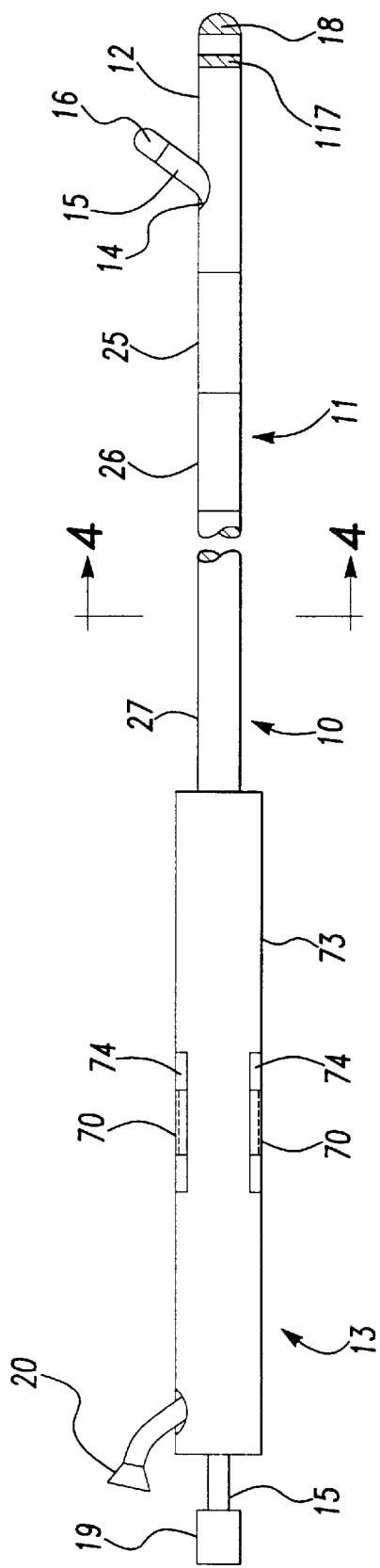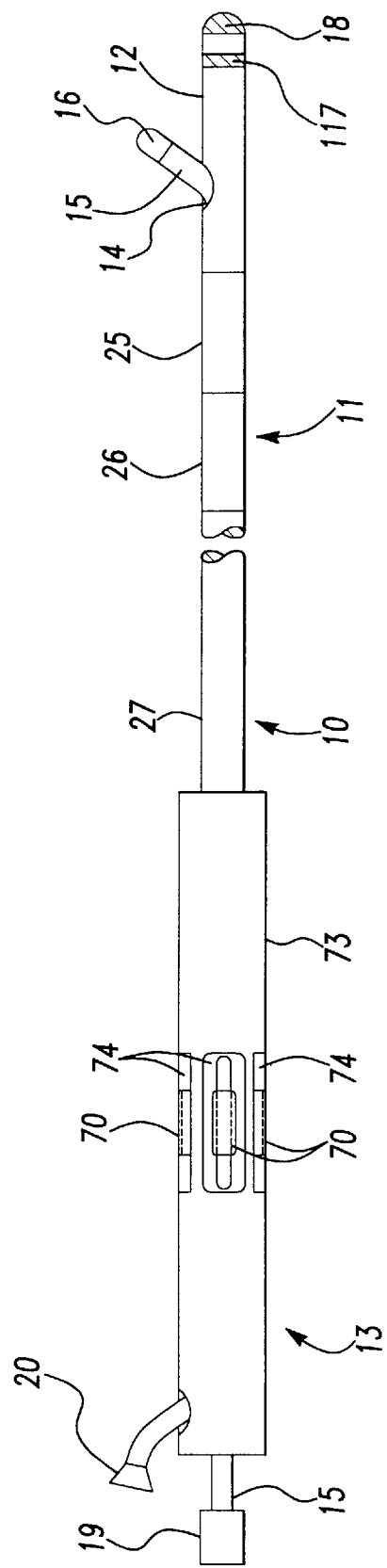

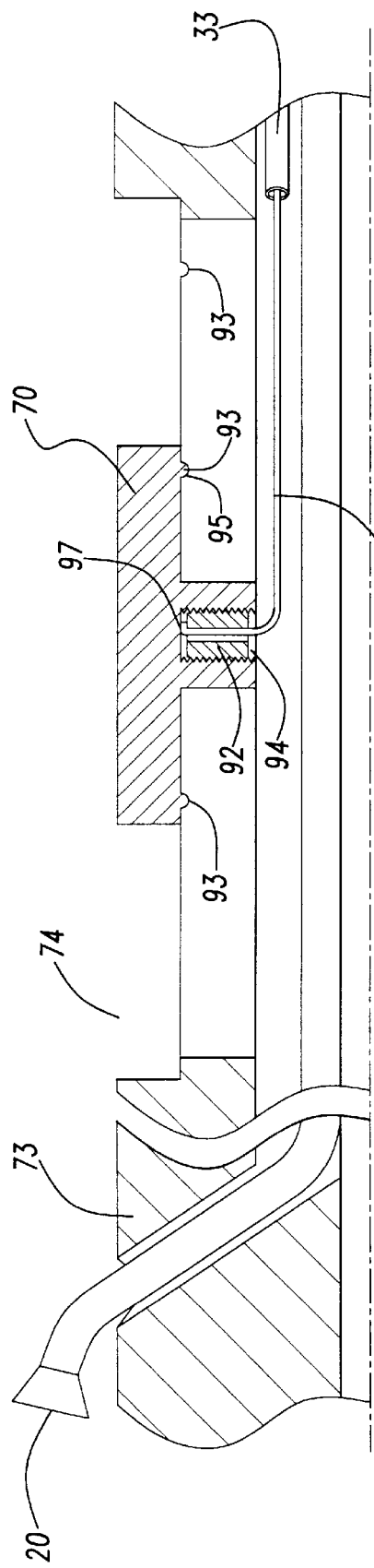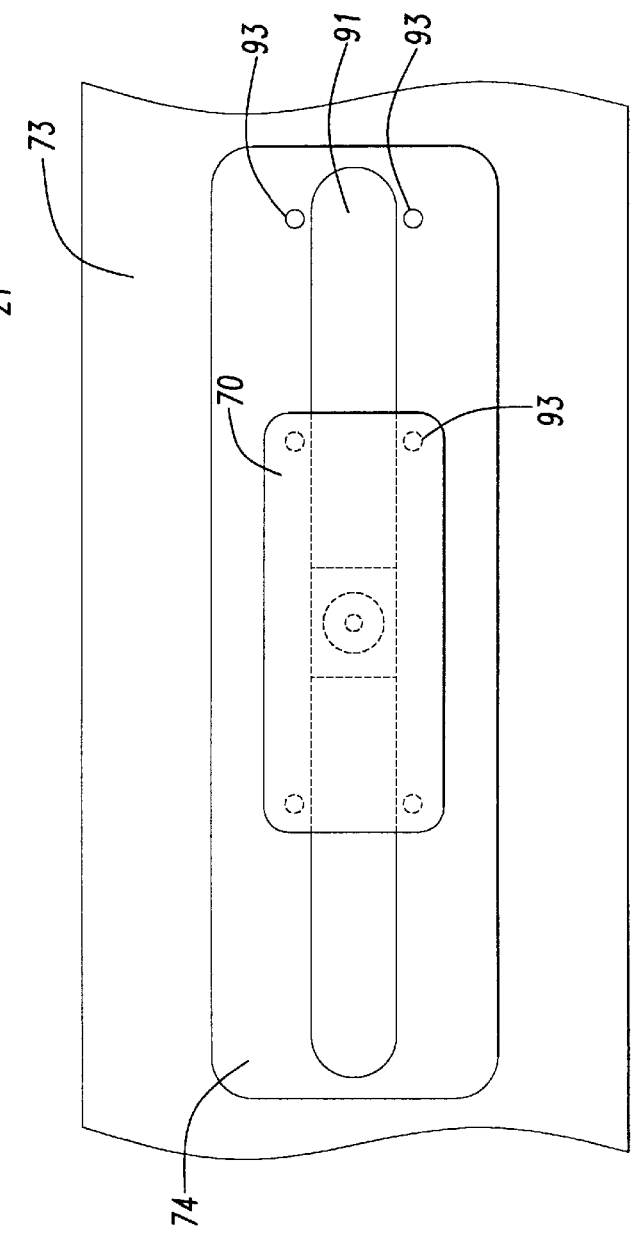

GUIDING CATHETER WITH ULTRASOUND IMAGING CAPABILITY

This application claims the priority benefit of Provisional Application No. 06/006,493 filed Nov. 9, 1995.

FIELD OF THE INVENTION

The present invention relates to a steerable guiding catheter with an ultrasound imaging capability. More specifically, the present invention relates to a steerable guiding catheter with an ultrasound imaging capability for endocardial deployment of an electrophysiology catheter.

BACKGROUND OF THE INVENTION

Aberrant accessory pathways can cause many forms of cardiac arrhythmias. Radio frequency (RF) ablation (the destruction of heart tissue by means of an electrode catheter) has been found to be a safe and efficacious means for treating arrhythmias caused by electrical accessory pathways between either atrium and ventricle or AV nodal re-entry circuits by interrupting accessory pathways.

To perform ablation, a special electrophysiology catheter is guided through an artery or vein into the patient's heart to the site of the accessory pathway to be ablated. The catheter is designed to transfer RF energy from an external source to the site of the accessory pathway in an amount sufficient to ablate the tissue. The ablated tissue is eventually replaced with scar tissue which interrupts the accessory pathway and the normal activity of the heart is thereby restored.

In an RF ablation procedure, RF energy is delivered to the ablation site and the endocardial tissue is sufficiently heated to form a lesion. Often, the sites of the accessory pathways tend to be relatively small and shallow. A typical ablation site is about 5–6 mm in diameter with a depth of about 3–5 mm. Standard electrode ablation catheters are capable of forming deep lesions in excess of that needed to form endocardial scar tissue. Extreme caution in their use is required, especially since there is always a risk of perforation of the myocardium during any such ablation procedure. Additionally, some accessory pathways are located deep within the myocardium near a cardiac artery or vein. Care must be taken when ablating these sites to prevent injury to the cardiac artery or vein or creation of a potential life threatening occlusion or perforation of an artery or vein. A catheter capable of visualizing an ablation site would be useful to locate and monitor the ablation site and thereby help minimize the risks involved.

Moreover, the anatomical position of an electrophysiology catheter is conventionally verified using fluoroscopic visualization techniques. A catheter comprising a visualization device would obviate or substantially minimize the necessity of fluoroscopic visualization as the anatomical position of such a catheter could be adequately realized during a procedure in relation to the surrounding cardiac chamber.

Finally, the successful ablation of an aberrant accessory pathway typically cannot be effectively verified and involves indirect verification using standard catheter mapping techniques. An electrophysiology catheter with visualization capabilities would be useful to enable an RF ablation to be completely visualized before, during and after the ablation and allow the lesion generated to be properly characterized.

Therefore, there is a need for a electrophysiology catheter with a visualization mechanism for visualizing the electrophysiology catheter ablation site.

SUMMARY OF THE INVENTION

The present invention is an electrophysiology guiding catheter with an ultrasound imaging capability for endocardial deployment of an electrophysiology catheter. The electrophysiology guiding catheter consists of a guiding catheter having a central lumen, a guiding catheter handle also having a central lumen, wherein the handle's distal end is connected to the guiding catheter's proximal end such that the lumens of the handle and catheter are coaxial and joined together. An electrophysiology catheter is guided within the guiding catheter and handle lumens. An ultrasound transducer is mounted on the guiding catheter's distal tip. An exit hole is defined toward the distal end of the guiding catheter to allow for the exit of the electrophysiology catheter tip.

The electrophysiology catheter tip comprises an electrode at its distal end for mapping and/or ablating endocardial tissue. The electrophysiology catheter is preferably steerable by longitudinal movement of a control handle relative to the body of the electrophysiology catheter. Conductive pathway signals can be received from the tip electrode and transmitted to a remote detector and display via a connector. RF energy can be transmitted to the tip electrode for ablating an aberrant conductive pathway.

Two puller wire guiding tubes are longitudinally embedded within the walls of the guiding catheter body and guiding catheter handle. Puller wires connected at the distal end of the guiding catheter body are guided within the puller wire tubes and exit proximate the distal end of the handle. There the puller wires are connected to thumb slides wherein movement of one thumb slide in a proximal direction causes the guiding catheter distal end to deflect in a direction toward the thumb slide and sliding of the other thumb slide proximally on the handle causes the guiding catheter distal end to deflect in the opposite direction.

The ultrasound transducer emits and receives energy in the form of ultrasound signals. The transducer is connected by cables running through the guiding catheter walls to a conventional ultrasound machine that provides an electronic transmission to the transducer for energizing the transducer to emit signals, and also displays the feedback received by the transducer on an appropriate display means.

The ultrasound transducer allows the cardiologist to properly image the area of the heart of interest. Specifically, the cardiologist, by viewing the images transmitted to a display, can learn about the depth of the myocardium of interest, other anatomical structures, and whether any cardiac arteries or veins are located nearby.

BRIEF DESCRIPTION OF THE DRAWINGS

FIG. 1A is a side view of an electrophysiology guiding catheter with ultrasound imaging capability with an electrophysiology catheter within the guiding catheter and two thumb slides for steering the guiding catheter;

FIG. 1B is a side view of an electrophysiology guiding catheter with ultrasound imaging capability with an electrophysiology catheter within the guiding catheter and four thumb slides (only three of which are shown) for steering the guiding catheter;

FIG. 6A is a cross sectional view depicting the upper half of a portion of the electrophysiology guiding catheter body having a thumb slide; and, FIG. 6B is a schematic top view of the portion of the electrophysiology guiding catheter body having a thumb slide.

DETAILED DESCRIPTION

Figure 2:
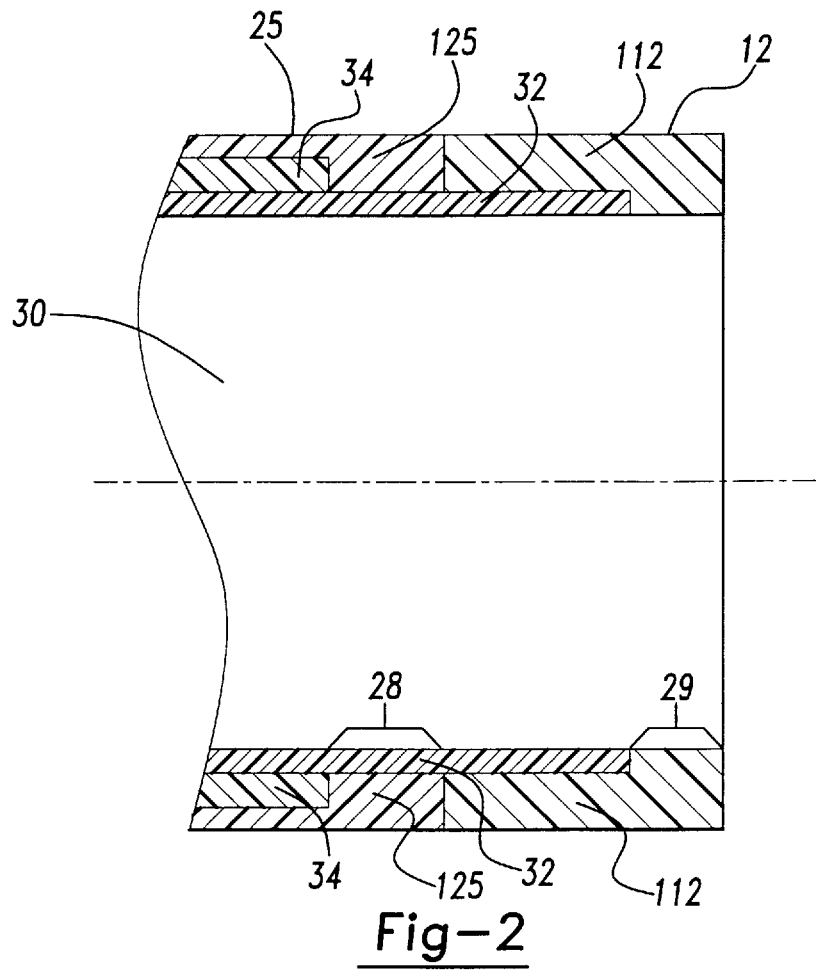
FIG. 2 is a cross sectional view of a portion of the catheter tip and a distal portion of the second transitional tip.

The present invention is an electrophysiology guiding catheter with an ultrasound imaging capability for endocardial deployment of an electrophysiology catheter. Referring to FIGS. 1A and 1B, a guiding catheter 10 constructed in accordance with the present invention is illustrated. It is suitable for use as a visualization mechanism for visualizing an endocardial ablation site and for simultaneously deploying an electrophysiology catheter for accessory pathway diagnosis and ablation.

The guiding catheter 10 comprises three primary components. The guiding catheter body 11 defines a central lumen 30 (shown and described with reference to FIG. 2) within which is guided an electrophysiology catheter 15. An ultrasound transducer 18 is fixedly attached to the distal end of the catheter body 11. In turn, the guiding catheter body 11 is fixedly attached at its proximal end to a hub 13 by conventional means.

An exit hole 14 is defined towards the distal end of the guiding catheter body 11 through which the electrophysiology catheter 15 exits the central lumen 30. The electrophysiology catheter 15 comprises a tip electrode 16 at its distal end for mapping and/or ablating endocardial tissue and is mounted at its proximal end to a control handle 19. Preferably, the electrophysiology catheter 15 is steerable by longitudinal movement of the control handle 19 relative to the body of the electrophysiology catheter 15. Aberrant conductive pathway signals can be received from the tip electrode 16 and transmitted to a remote detector and displayed via a molded electronic connector 20. RF energy can be transmitted to the tip electrode 16 via a remote RF source also connected to the molded connector 20. An exemplary example of an electrophysiology catheter suitable for use with the present invention is a steerable open lumen catheter as described in U.S. Pat. No. 5,431,168 issued to Wilton W. Webster, Jr. on Jul. 11, 1995 and manufactured by Cordis Webster, Inc., Baldwin Park Calif., the disclosure of which is incorporated herein by reference. However, many other electrophysiology catheter could be used.

The guiding catheter body 11 can be of any suitable length for intravascular insertion. In the described embodiment, a length of about 100 cm is used. Similarly, the exit hole 14 can be of any suitable size to allow an electrophysiology catheter to exit the guiding catheter body 11. In the described embodiment, a size of 0.04±0.03 inches is used and the distance between the distal edge of the exit hole 14 and the distal end of the catheter tip 12 is approximately 2.5 cm.

An ultrasound transducer 18 is fixedly attached to the distal end of the guiding catheter body 11. The transducer 18 emits and receives ultrasound in a single direction in the same manner as a transesophogeal ultrasound unit. In addition, other visualization devices can be employed, such as those used for endoscopy. The exact dimensions of the transducer 18 are not critical and any transducer of suitable construction can be employed. Preferably, the transducer is cylindrical with a rounded tip approximately 1 to 2 cm in length and has an outer diameter of about 12 to 12.5 French so as to form a continuous outer surface with the guiding catheter body 11. In the described embodiment, an ultrasound transducer with a 64 element crystal and having an outer diameter of 12 to 12.5 French is employed. Exemplary examples of an intra-lumen ultrasound transducers suitable for use with the described invention are manufactured by Endosonics, or by Acuson, Inc., Mountain View Calif.

The guiding catheter body 11 comprises four main sections as follows (from proximal to distal end): a main body 27, a first transitional tip 26, a second transitional tip 25 and the distal catheter tip section 12. Each of these four sections can be of any suitable construction and dimensions.

In the described embodiment, the four sections each comprise several layers (described further herein below) of which some are described in U.S. Pat. No. 5,045,072 to Castillo et al., and U.S. Pat. No. 4,531,943 to Van Tassel et al., the subjects of which are incorporated herein by reference. Each section has an outer jacket. The four sections cooperate to allow the guiding catheter 10 to be maneuvered through a patient's vascular system and deflected once situated within the heart. Consequently, each outer jacket has a different derometer (D) hardness as follows: the main body 27 is about 65 D; the first transitional tip is about 55 D; the second transitional tip is about 40 D; and the catheter tip is 80 AE. Preferably, with the exception of the catheter tip 12, the outer jacket is constructed of nylon having the aforementioned hardness. The catheter tip 12 can be made from a polyether polyurethane formulation as described in U.S. Pat. No. 5,045,072 to Castillo et al.

Referring to FIG. 2, a cross-sectional view of the catheter tip 12 and a distal portion of the second transitional tip 25 are shown. For simplicity, the exit hole 14 has been omitted. A central lumen 30 is defined longitudinally through the guiding catheter body 11. An inner liner 32 runs the length of the guiding catheter body 11 ending slightly proximal to the end of the catheter tip 12 to define a distal catheter tip joint section 29. In the described embodiment, the width of the distal catheter tip joint section 29 is approximately 0.04±0.03 inches and the inner liner 32 is preferably constructed of polytetrafluoroethylene (PTFE), also known as Teflon.

A braided wire sleeve 34 also runs the length of the guiding catheter body 11 but only up through the second transitional tip 25, ending slightly proximal to the end of the second transitional tip 25 to form a proximal catheter tip joint section 28. In the described embodiment, the width of the proximal catheter tip joint section 28 is approximately 0.04±0.03 inches and the braided wire sleeve 34 is preferably constructed of stainless steel.

Figure 3:
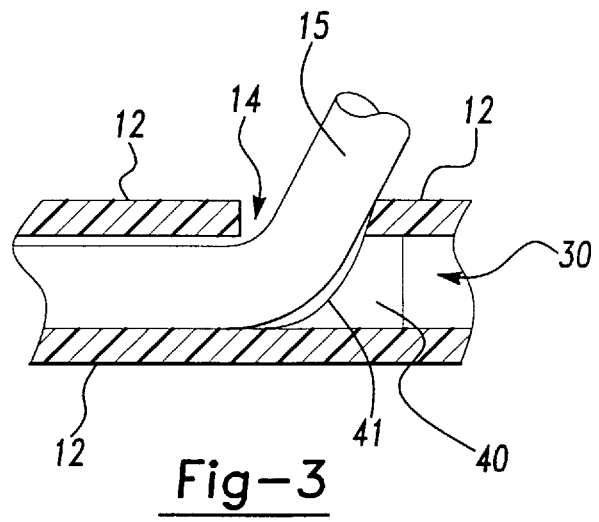
FIG. 3 is a longitudinal cross sectional view of the catheter tip depicting the electrophysiology catheter exit hole.

Referring to FIG. 3, a cross sectional view of the catheter tip 12 showing the exit hole 14 is shown. A deflector 40 is located beginning at the distal edge of the exit hole 14 and continuing towards the opposite wall of the catheter tip 12 in the proximal direction to thereby form an inclined surface 41. The deflector 40 causes the electrophysiology catheter 15 to deflect and exit the catheter tip 12 when traveling distally relative to the guiding catheter body 11.

The deflector 40 can be of any suitable construction and in the described embodiment has approximately the same outer diameter as the central lumen 30. Also, the deflector 40 is preferably constructed of a smooth plastic material such as PTFE or polyurethane. The inclined surface 41 can be at an angle suitable for deflecting the electrophysiology catheter 15. In the described embodiment, the angle for deflection is from about 10 degrees to about 60 degrees.

Figure 4:
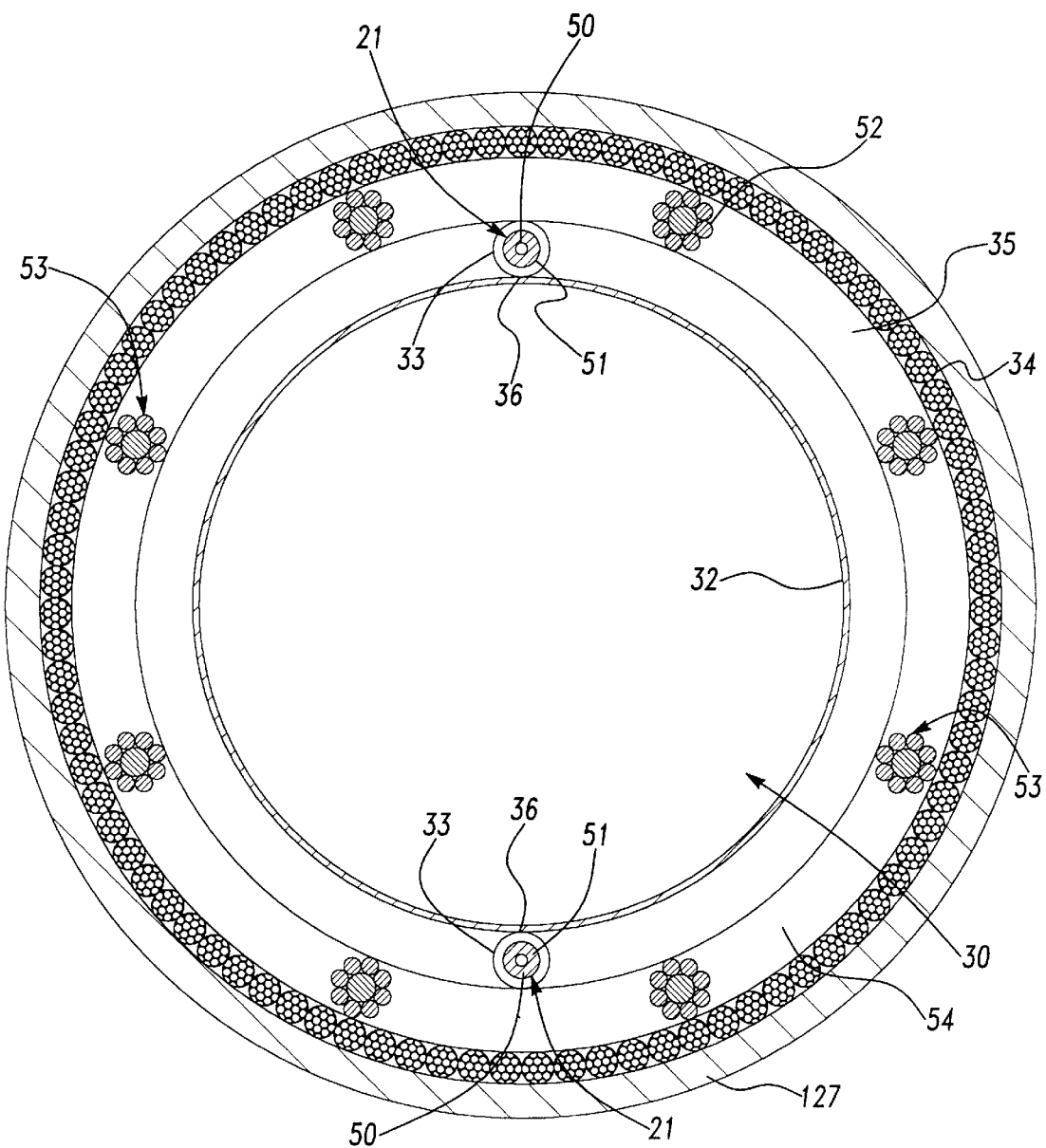
FIG. 4 is a cross sectional view of the guiding catheter body.

A cross sectional view of the guiding catheter body 11 taken along line 4—4 of FIG. 1 is shown in FIG. 4. With the exceptions as indicated herein, the construction of each of the four sections comprising the guiding catheter body 11 is substantially similar and involves the following layers. The innermost layer is an inner liner 32, preferably constructed of PTFE, and defining a central lumen 30 running longitudinally its entire length.

Figure 5:
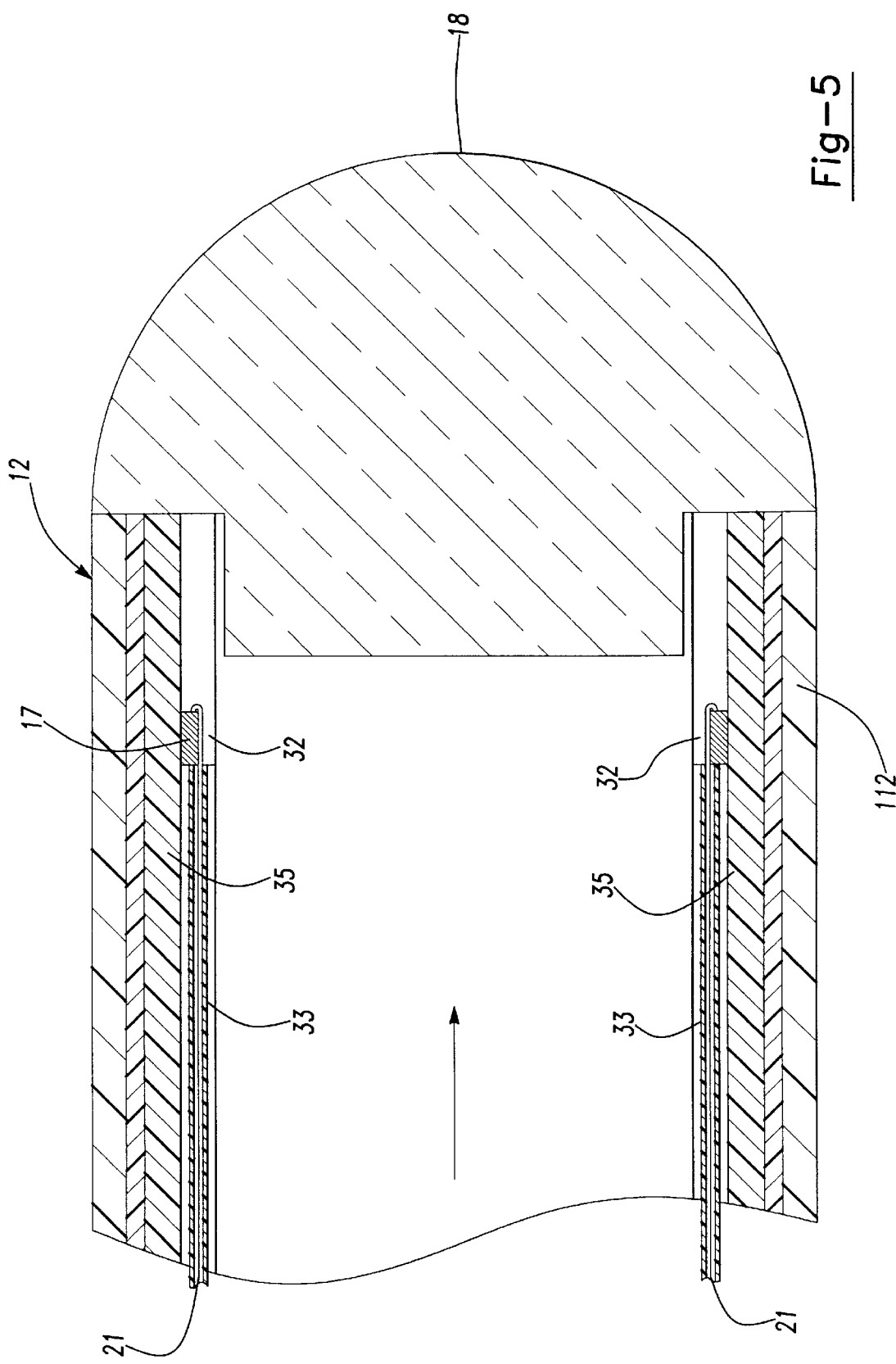
FIG. 5 is a longitudinal cross sectional view of the electrophysiology guiding catheter body tip.

In the described embodiment, the central lumen 30 has an inner diameter of about 0.110 inches. Preferably, the inner liner 32 defines two longitudinal grooves 36 on its outer surface at opposite sides from each other. A pair of small puller wire tubes 33 are situated in the grooves 36 to maintain their orientation. Preferably, the puller wire tubes 33 are constructed of polyamide with an inner diameter of approximately 0.012 inches. Puller wires 21 run axially within the puller wire tubes 33. The puller wires 21 (not shown in FIG. 4 for clarity, but are shown in FIGS. 5 and 6) have a diameter of about 0.01 inches. As illustrated in FIG. 6, the puller wires 21 are constructed of stainless steel cable 50 with a PTFE sleeve 51 covering them to provide lubricity within the polyamide tubes 33.

A layer 35 of eight braided ribbon cables 53 run longitudinally along either side of the puller wire tubes 33 and arranged to surround the inner liner 32. In the described embodiment, the 64 element crystal for the ultrasound transducer 18 requires 64 lead wires. Thus, the braided ribbon cable layer 23 preferably comprises eight ribbon cables bundled together and each having eight individual microcoax wires 52 of about 8 mils thickness. The braided wire sleeve 34 runs longitudinally over the puller wire tubes 33 and the braided ribbon cables layer 35. Preferably, the braided wire sleeve is constructed of stainless steel. Finally, the above-described outer jacket 127, preferably constructed of nylon, surrounds the braided wire sleeve layer 34.

Referring to FIG. 5, a longitudinal cross sectional view of the guiding catheter body tip 12. The transducer 18 is fixably attached to the distal end of the catheter body 12 by conventional means. A circular marker band 17 is also fixedly attached about the catheter tip 12 at a slight distance proximal to the catheter tip 18. In the preferred embodiment, the marker band is embedded between the inner liner 32 and the cable layer 35. The marker band 17 is for assisting a practitioner in locating the orientation of the catheter tip within a patient's body. In the described embodiment, the marker band 17 is about 1 cm from the end of the transducer 18. The marker band 17 can be of any suitable construction, however, in the described embodiment, platinum or a platinum-iridium alloy is used. In a preferred embodiment, the marker band also serves as a location for mounting the puller wire ends as described below. In an alternate embodiment, the marker band 117 may be fixedly attached to the outer surface of the catheter tip as shown in FIG. 1A.

The catheter tip 12 is steerable using the pair of puller wires 21. To aid in steering, each of the puller wires is connected to a thumb slide 70 which is slidably mounted on the outer surface of the handle, preferably proximate to its distal end (FIGS. 1, 6A, 6B). The pair of thumb slides are positioned opposite each other on the handle 73. Preferably, the slides are positioned within recessions 74 on the handle outer surface.

Sliding of the thumb slides in the proximal direction relative to the catheter pulls on the puller wire to which it is connected and causes the catheter tip 12 to deflect in a horizontal direction. The deflection is such that the catheter tip 12 becomes concave on the side of the puller wire that was moved proximally. Reverse deflection of the catheter tip occurs by sliding the opposite thumb slide proximally relative to the guiding catheter. Deflection of the catheter tip 12 is required to align the ultrasound vector beam for accurately visualizing the ablation site. Consequently, bidirectional movement in a left-right horizontal plane is achieved using the thumb slides 70 which are connected to puller wires 21. In the described embodiment, the catheter tip 12 is capable of 1 to 4 movement degrees of freedom. As it would become obvious to one skilled in the art, the embodiment comprising a single puller wire only requires a single thumb slide.

In FIGS. 6A and 6B, the puller wires 21 are preferably connected to the thumb slides via a set screw 92. The set screw 92 is threaded inside the thumb slide 70 through an opening 94 on the thumb slide bottom. Each puller wire 21 exits its tube 33 and is routed through a central orifice 96 on the set screw so that a portion 97 of the wire 21 protrudes beyond the set screw. The set screw is then threaded onto the thumb slide until it jams the wire portion 97 extending beyond the set screw against the thumb slide, thereby forming a connection between the puller wire and the thumb slide.

Each thumb slide slides within a slit 91 formed on each recession 74 on the handle. Pairs of depressions 93 are formed on the recession 74 on either side of the slit. A pair of protrusions 95 extending from a bottom surface of the thumb slide engage a pair of the depressions and lock the slide in position. Extra force must be applied against the thumb slide to disengage it from the depressions. The depressions are strategically located to lock the thumb slide in a distal, proximal or intermediate position.

Additionally, in a further embodiment (not shown), two additional puller wires and two additional puller wire polyamide tubes are located 90° relative to the left-right puller wires 21 to enable movement of the catheter tip 12 in an up-down (vertical) plane. The additional puller wires are connected to two additional thumb slides which are located at 90° relative to the other two thumb slides.

The central lumen 30 is capable of accepting an electrode electrophysiology catheter 15 fed in from the distal end of the hub 13. In the described embodiment, an electrophysiology catheter with an eight French outer diameter is preferred.

Construction of the guiding catheter body 11 is as follows: First, the inner liner 32 is placed on a mandrel. The pair of longitudinal grooves 36 are formed 180° apart along the length of the inner liner 32. The pair of puller wire tubes 33 are placed within the longitudinal grooves 36. The braided ribbon cables 53 are pulled and placed in position over the inner liner 32. The braided ribbon cables layer 23 is completed by the addition of a flexible filler material 54, preferably a plastic such as polyurethane or similar material. The braided wire sleeve 34 is pulled over the assembly and the appropriate outer jacket 35 is pulled over the braided wire sleeve 34 to complete construction. The entire assembly is removed from the mandrel and, using a vertical fusing device, the outer jack 35 is heat shrunk into place.

In use, a cardiologist would advance the guiding catheter 10 with the electrophysiology catheter 15 inside the assembly from a remote site such as the femoral artery or vein into the heart. The cardiologist would have the ultrasound transducer connected to a conventional ultrasound machine that provides the needed electronic transmission to the transducer and displays the feedback from the transducer on an appropriate display means. The cardiologist would constantly monitor the position of the guiding catheter as it advances into the heart.

Once the guiding catheter is in a heart chamber of interest, either an atrium or a ventricle, the cardiologist would then advance the electrophysiology catheter distally relative to the guiding catheter such that the electrophysiology catheter exits out the exit hole and moves distally past the transducer. The cardiologist would use the steering means of the electrophysiology catheter to steer the catheter tip appropriately. As apparent from the drawings, the electrophysiology catheter exits from the guiding catheter at an angle away from the guiding catheter that is the same angle as the deflector. The cardiologist would steer the electrophysiology catheter back towards the guiding catheter as the electrophysiology catheter is advanced distally. Additionally, the cardiologist would use the puller wires in the guiding catheter to steer the guiding catheter in a direction towards the electrophysiology catheter. Eventually, the cardiologist would have the electrophysiology catheter in line with the transducer of the guiding catheter such that the ultrasound display means displays the location of the electrophysiology catheter within the heart chamber of interest.

The cardiologist would the electrically map areas of the endocardium to precisely locate the accessory pathways with the electrophysiology catheter. Once an accessory pathway has been identified and properly mapped, the cardiologist wold use the ultrasound transducer of the guiding catheter to properly image the area of the heart. The cardiologist can then learn about the depth of the myocardium at interest, other anatomical structures, and whether any cardiac arteries or veins are located nearby. Once proper ultrasound imaging has been performed, the cardiologist would then place the distal tip electrode of the electrophysiology catheter at the ablation site. RF energy would then be delivered to the distal tip electrode of the electrophysiology catheter for an appropriate amount of time. The ablation of the heart tissue would also be constantly monitored by the cardiologist using the ultrasound transducer, the area of tissue death being observable. This way the cardiologist can apply enough RF energy to ablate the accessory pathway, but still limit the amount of RF energy to prevent overablation which can cause cardiac perforation or thrombosis of a vessel near by.

Thus, the present invention provides a particularly useful safety feature in that a cardiologist using the ultrasound imaging of the guiding catheter while performing ablation with the electrophysiology catheter would prevent making lesions that are too deep, would prevent surface epicardial vessel thrombosis due to heating a cardiac artery or vein, would prevent cardiac perforation from ablating the entire thickness of the heart wall, and would verify that an ablation is occurring or has taken place.

Although this invention has been described in certain specific embodiments, many additional modifications and variations will be apparent to those skilled in the art. It is, therefore, understood that within the scope of the appended claims, this invention may be practiced otherwise then specifically described.

What we claim is:

1. A steerable guiding catheter having an ultrasound imaging distal tip in combination with an electrophysiology catheter comprising:

an elongated tubing body having a proximal end and a distal end and defining a lumen extending for substantially the entire length of the tubing body for receiving an electrophysiology catheter;

an elongated, flexible electrophysiology catheter slidably disposed within said lumen, a flexible tip portion attached to the distal end of the tubing body;

an ultrasonic transducer mounted on the flexible tip portion of the tubing body to transmit ultrasound energy and receive resultant echoes so as to provide visualization of an ablation site;

an electrical conductor disposed in the tubing body for electrically connecting the ultrasound transducer to control circuitry external of the steerable catheter;

second and third lumens extending lengthwise through the tubing body and both being offset from the central axis of the tubing body;

first and second puller wires extending through and slidable disposed in said second and third lumens, respectively, each said puller wire being fixedly attached to distal end of the flexible tip portion at a position on opposite sides of the central axis of the tubing body; and, control means attached to the proximal ends of the puller wires for moving the puller wires longitudinally relative to the catheter body to thereby deflect the flexible tip portion of the guiding catheter.

2. A combination steerable catheter and electrophysiology catheter as defined in claim 1, wherein the tubing body includes:

a fourth lumen extending lengthwise through the tubing body and being offset from the central axis of the tubing body; and, the electrical conductor extends through the fourth lumen and is connected to the ultrasonic transducer.

3. A combination steerable catheter and electrophysiology catheter as defined in claim 2, wherein the tubing body comprises a main body portion, a first transitional portion being of a lower durometer than the main body portion extending distally from the main body portion, a second transitional portion being of a lower durometer than the first transitional portion and extending distally from the first transitional portion, and the flexible tip portion being of a lower durometer than the second transitional portion and extending distally from said second transitional portion.

4. A steerable guiding catheter as defined in claim 3, wherein the electrophysiology catheter takes the form of an ablation catheter.

5. A steerable guiding catheter as defined in claim 4, wherein wherein the electrophysiology catheter takes the form of a cardiac mapping catheter.

6. A combination steerable catheter and electrophysiology catheter as defined in claim 1, wherein the tubing body includes at least eight conductor lumens extending lengthwise through the tubing body and each being offset from the central axis of the tubing body; and, at least eight electrical conductors extend through and are disposed in each conductor lumens and are each connected to the ultrasonic transducer.

* * * * *